United States Patent [19]

Chemaly

[11] Patent Number: 4,972,493
[45] Date of Patent: Nov. 20, 1990

[54] METHOD FOR INSPECTION OF SURFACES
[75] Inventor: Ephrem A. Chemaly, Austin, Tex.
[73] Assignee: Motorola, Inc., Schaumburg, Ill.
[21] Appl. No.: 140,704
[22] Filed: Jan. 4, 1988
[51] Int. Cl.$^5$ .............................................. G06K 9/00
[52] U.S. Cl. ........................................ 382/8; 382/41
[58] Field of Search .................... 382/1, 8, 30, 33, 34, 382/41, 48, 49; 364/488; 358/101, 106, 107; 356/388, 392, 394

[56] References Cited
U.S. PATENT DOCUMENTS

| | | | |
|---|---|---|---|
| 4,644,585 | 2/1987 | Crimmins | 382/41 |
| 4,665,551 | 5/1987 | Sternberg et al. | 382/41 |
| 4,672,562 | 7/1987 | Egli et al. | 364/559 |
| 4,811,410 | 3/1989 | Amir et al. | 382/8 |

Primary Examiner—David K. Moore
Assistant Examiner—Jose L. Couso
Attorney, Agent, or Firm—John A. Fisher; Jasper W. Dockrey

[57] ABSTRACT

An automatic system for the inspection of surfaces of an object employing computer vision. The system examines the uniformity of the surface and adds it to the negative of an ideal mask, and then thresholds the result to determine if the object is defective or not. A binary image showing only the defects is generated by the system. The system ignores surface features, such as locating notches or markings that are intentional, by "fitting" them with their morphological negatives. Small electronic packages, such as integrated circuit plastic packages (e.g. dual-in-line packages or DIPs), can be accurately inspected by the system. The system provides an objective, fast and economical method of inspecting objects.

9 Claims, 3 Drawing Sheets

METHOD FOR INSPECTION OF SURFACES

CROSS-REFERENCE TO RELATED APPLICATION

This application is related to co-pending patent application Ser. No. 07,140,705, relating to the automatic inspection of protruding features of objects, filed of even date.

1. Field of the Invention

The invention relates to automatic inspection systems, and in particular relates to the automatic visual inspection of the surfaces of objects.

2. Background of the Invention

In the competitive production of products, it is common to inspect the products with respect to performance, physical integrity, physical dimensions, cosmetic appearance, etc. before the products are sold. As competition becomes tighter, manufacturers move from classical manual labor intensive methods to more sophisticated techniques using automation. One of the newest techniques of automatic inspection or quality control is to use computer vision techniques by which a computer receives data from an optical system and processes the data to determine if a particular product passes inspection.

While electronic devices have long been tested internally by high-speed automatic testing and handling equipment, computer vision inspection systems are now being developed to inspect the outside of electronic packages. This task has proven considerably more difficult than testing the interior circuitry. Ideally, such systems should inspect both the package body and the leads that extend from the package body.

Developing an automated visual inspection system for a particular device requires careful design. First, there must be an objective, quantifiable visual test standard for the part. Commercial general purpose inspection systems are not trainable by presenting them with a collection of good and defective parts and a few general words of guidance. Second, the inspection requirements are used to specify the image acquisition parameters, such as lighting, background, the required image resolution. Very important is the size of the digital image sent to the computer. The greater the digital image, the larger the number of bits that must be stored and manipulated by the computer or processor, which slows the inspection time.

Third, an image analysis strategy must be designed, processing algorithms developed, and a classification scheme defined. Fourth, an appropriate parts handling mechanism is needed to present the parts to the vision system. Of course, the performance of any computer inspection system must be measured by comparing its results with the independently and presumably accurate parts classification prepared from the existing manual inspection.

However, the demonstration of a satisfactory method for inspecting a particular electronic package is not, by itself, a sufficient basis to use an automatic inspection system. For a production machine to be implemented, the inspection system must also meet cost, speed, reliability, and size constraints, as well as ease of integration with existing production methods.

It is only when all of the above requirements have been considered that a successful implementation of an automated visual inspection system can be achieved. In addition, it would be desirable if a particular inspection system could be readily adaptable to various electronic device packages.

Conventionally, a visual inspection of the bodies of the packages is undertaken to reject the parts with surface flaws, such as bubbles, blisters, chips, cracks, voids and grease marks. Since all of these flaws are inspected by humans, it is apparent that this inspection involves subjective measurement. As the emphasis on quality increases, it becomes more difficult for human operators to consistently and quickly inspect products for what are often cosmetic flaws with objective consistency. Thus, another goal of an automatic inspection system is to inspect package bodies consistently according to a precise, objective standard. An automatic inspection system should also ideally be able to be adapted to inspect the surfaces of other objects, besides electronic packages.

SUMMARY OF THE INVENTION

Accordingly, it is an object of the present invention to provide an automatic, optical inspection system that can inspect the surfaces of objects for flaws and defects such as bubbles, blisters, chips, cracks, voids and grease marks.

It is another object of the invention to provide an automatic, optical inspection system that implements objective, quantifiable visual test standards for the surface of a particular part type.

Another object of the present invention is to provide an automatic, optical inspection system that is superior to manual inspection of the surfaces of objects, such as the surfaces of bodies of electronic packages and other objects having surfaces that must meet certain specifications.

Still another object of the present invention is to provide an automatic, optical inspection system that may be easily integrated with existing production methods.

In carrying out these and other objects of the invention, there is provided, in one form, a method for inspecting a surface of an object to determine whether the object meets a predetermined standard, involving first individually providing the objects having surfaces to be inspected to an inspection station. The surface should be illuminated by a low angular light source, and an imaging device, such as a camera, perceives a gray scale image of the illuminated surface. Next, the gray scale image is added to an ideal mask and then a binary image is generated showing the defects of the surface, if any. Then it is determined whether the defect areas on the binary image with defects are larger than a predetermined specification under the predetermined standard. Finally, the objects having surfaces that meet the predetermined specification are sorted from the objects having surfaces that do not meet the predetermined specification.

DETAILED DESCRIPTION OF THE INVENTION

A new method for automatically inspecting the surface of an object which uses computer vision has been discovered. The system is particularly suited for inspecting the surfaces of an electronic package. Such surfaces are examined for the presence of structural and cosmetic defects such as pits, holes, blisters, grease marks, chips, cracks, etc.

In a particular application, the term computer vision describes a discipline which may include the study of optics, imaging, image processing, pattern recognition, artificial intelligence, etc.

During the course of the description of the invention, as an example only, the object to be inspected is an electronic package, typically being a six-sided polyhedron with only rectangular sides, where the sides are generally flat. Of course, other types of objects, packages and surfaces may also be inspected using the method of this invention.

For purposes of illustration only, the object to be inspected will be taken to be a dual in-line package or DIP, as an example of a package that is well-known in the art. It is anticipated that other package configurations, such as plastic leaded chip carriers (PLCCs) and pin grid arrays (PGAs), among others, could also be inspected using the invention after the physical equipment is rearranged by one skilled in the art following the principles of the invention. Indeed, other objects with surfaces could be inspected with an analogous system. The inventive system is particularly suited for examining flat surfaces, particularly those with a fine to rough surface texture, in contrast to a very smooth surface.

OVERALL VISION SYSTEM

Figure 1:
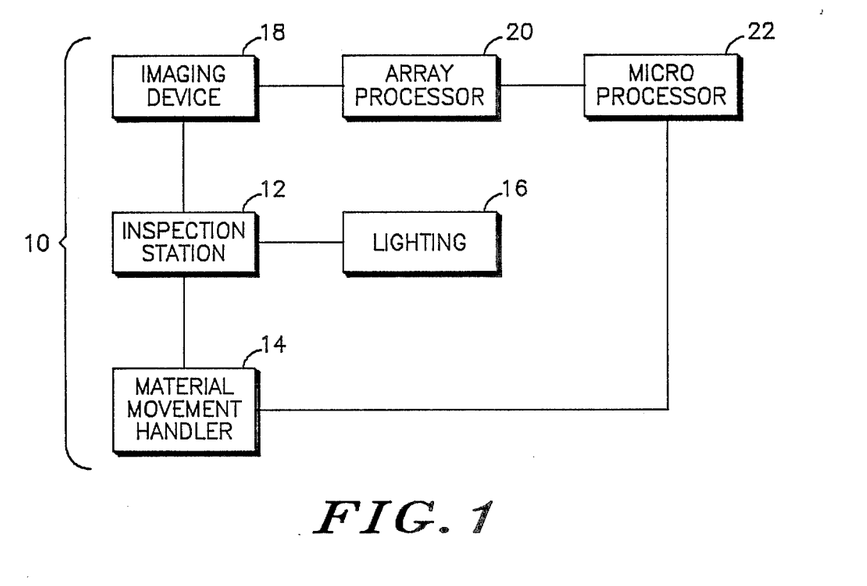
FIG. 1 is a block diagram of the various major parts of the inspection system of the present invention.

Shown in FIG. 1 is a block diagram of the vision system 10 of the present invention. The electronic packages to be inspected are brought individually to an inspection station 12 by the material movement handler 14. A lighting system 16 illumines the features of the object to be inspected, here the surface of the DIP, and a picture of the object is taken by the imaging device 18, such as a camera. The video signal produced by the imaging device 18 is then digitized and stored in a two dimensional array. The array may be any suitable size, but in the particular embodiment to be described, the array is a 512×512 array using 8-bit data. This array gives a quarter megabyte (262,144 bytes) worth of information, which is a considerably large amount of information to process. In image processing, each piece of data is referred to as a picture element, or "pixel". This data needs to be segmented by an array processor 20 which presents the relevant information to a microprocessor 22 that can then analyze this information and decide whether the object or package being inspected is defective or not. In turn, microprocessor 22 sends a "good" or "reject" signal to the material movement handler 14 which then sorts the part into the appropriate bin. Reliable acquisition and accurate positioning of the part to be inspected by the material movement handler 14 can greatly reduce the complexity of other system processes. In image analysis, for example, if the part location is not well known, a large amount of time is needed to locate the part before the inspection can be performed. This mechanical system must operate reliably for extended periods of time.

INSPECTION STATION AND LIGHTING SYSTEM

During the manufacture of DIP integrated circuits (ICs), the surfaces of the parts are inspected to assure that they do not contain defects. Conventionally, this has been done by human operators looking at the bodies of the packages. If an operator believed that a package contained a defect of any kind, it is usually discarded. However, as quality standards are improved, some small defects that are difficult to detect may require disqualifying the part or may permit it to meet the standard, depending on the kind of defect. For example, a single, very small pit is usually not enough to disqualify a part, however, many small pits close to each other is a type of defect requiring rejection. Also, such visual inspection is time consuming and requires the operator to manipulate the part for several seconds to permit the light to illuminate the surface in just the right way. It is apparent that this inspection involves considerable subjective measurement. The inventive vision system provides an objective inspection technique that is faster, less expensive and more reliable than the conventional method.

It was surprisingly discovered that a crucial part of the vision system was the design of the inspection station 12 and the lighting system 16 used therewith. It was found that the vision system would work best if only low angular light is used to illuminate the surface to be inspected.

Figure 2:
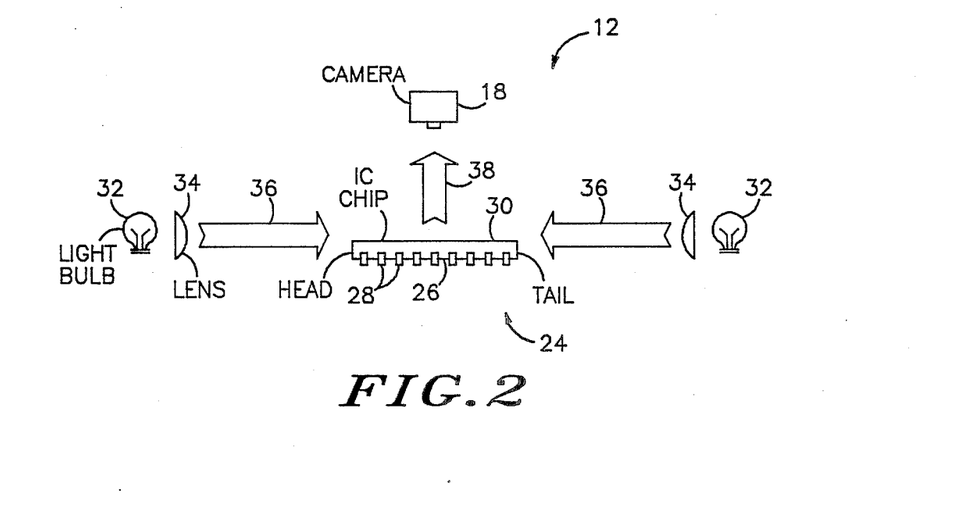
FIG. 2 is a side view of the surface illumination station that is part of the inspection system of the present invention.

Shown in FIG. 2 is the lighting configuration determined to be the best, showing the inspection station 12 and an integrated circuit DIP 24 seen from the side. DIP 24 has a package body 26 from which a plurality of leads 28 extend therefrom and turn downward in the same direction on both sides of body 26. The surface 30 of the DIP 24 being inspected should be illumined from the side by light sources 32 by direct light 36 on the surface 30. The reflected light 38 is perceived by the imaging system or camera 18. One of the drawbacks of low angular lighting is that the light intensity decreases as the inverse square of the distance of propagation. To solve this problem, the light sources 32 are focused with convex lenses 34 which creates a uniform parallel beam.

It is suggested that two light sources be used to provide semi-uniform light across the package. Placing light sources 32 on both sides of the DIP 24 may present a problem in presenting the inspection station 12 in a small space. Thus, mirrors may be used to create virtual images of the lights where it is physically impossible to mount them. Such a system also reduces the number of light sources needed.

To understand why this system works, the nature of the surface 30 being studied must be understood. All surfaces have some sort of texture, even those perceived as very smooth. The smoother the surface, the finer the texture. For example, the surface of the typical DIP has a mat surface texture that can be perceived only microscopically as a series of tiny bumps. Such a surface will reflect a given frequency of light at a given angle with a particular intensity. Defects on the surface such as pits or holes reflect very little light back into the camera because they are shaded by the surrounding surface. A blister or bubble behaves like a specular surface, that is, mirror-like and will reflect light at the same angle as the incident light (with a negative sign) and thus will not reflect it back to the camera 18. A grease mark will also appear as a dark area because the liquid grease will fill the small uniform voids between the uniform bumps of the surface texture and make the surface smoother or more specular than the surrounding surface. Thus, the light will be scattered from the grease mark in a different direction from that of the rest of the surface and the grease mark will appear dark.

A white graphic mark is a smooth surface on the relatively dark, mat surface virtually reflects all light frequencies in all directions. The intensity of the reflected light is high and the mark is seen by the camera as a bright area.

It is anticipated that the system of this invention could be employed to inspect rougher surfaces and smoother surfaces than those of a plastic DIP body, however, the surfaces must be uniformly rough or smooth and the sensitivity of the system may have to be adjusted. For example, with a smooth surface, if the grayscale value of the defect approaches the gray scale value of the uniform texture, the defect may be difficult to detect.

In summary, with low angular lighting, the mark is seen by the camera as a bright area, the regular, intended surface depressions and defects, are seen as dark areas, and the remaining surface is of intermediate brightness. As an example, for comparison purposes using a gray scale between 0 and 255 (using an 8-bit or $2^8$ value scale), the mark may have a value around 200, the depressions have a value around 70, and the remaining surface has a value around 150.

IMAGE FROM INSPECTION

Figure 3:
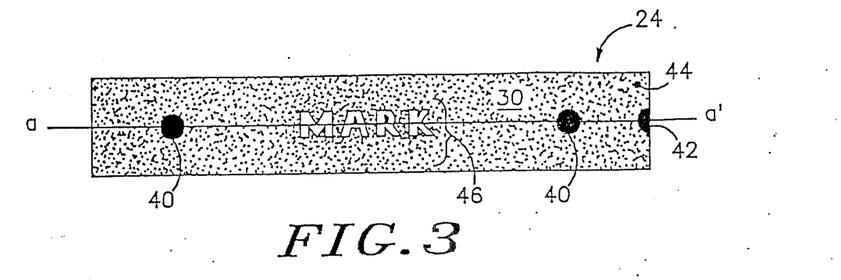
FIG. 3 is a top view of the surface being inspected using the system of this invention as it might be perceived by an imaging device.
Figure 4:
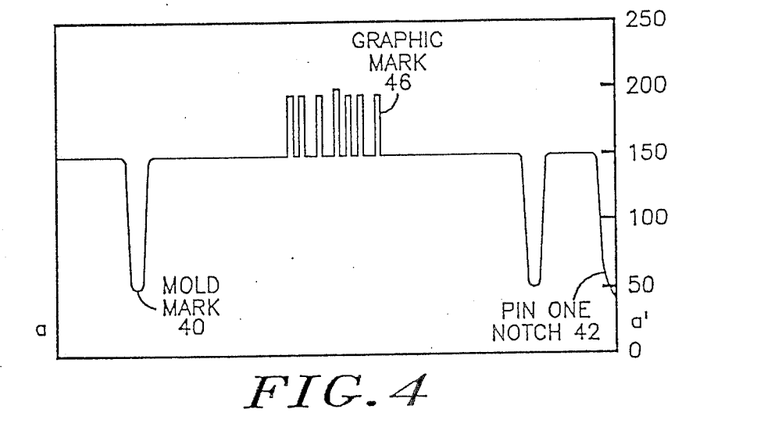
FIG. 4 is a chart of gray scale intensities across the surface being inspected as a function of the length of the surface on the line a-a' of FIG. 3.

FIG. 4 is a profile of the image of the top surface 30 of FIG. 3 taken along line a–a' using the gray scale just discussed. It can be seen that the areas of darkness, the mold marks 40 and pin one notch 42 are low on the gray scale, the graphic mark 46 is relatively high on the gray scale, while the remainder of the package surface 30 has an intermediate value. The image of FIG. 4 is the gray scale image.

FIG. 3 is an illustration of how the top surface 30 of a DIP 24 might appear to the imaging device 16. Most of the surface 30 appears as the intermediate gray, while intentional mold marks 40, pin one notch 42 and optional pin one dimple 44 appear as dark areas and the graphic mark 46 in the center of the surface appears as a bright area. Chips, holes, pitted surfaces, etc. are depressions shaded by the surrounding areas, and they are seen as dark features like the mold marks 40. A blister is a raised specular shape also seen as a dark area except for a bright ring inside of it. A grease mark is also a specular area seen as a dark area by the imaging device 18. See FIG. 7, for example. Dust and powder on the surface 30 of DIP 24 are seen as bright spots. However, dust and powder are not considered defects inasmuch as they can be easily removed. Thus the defects that require the object 24 to be rejected are perceived as dark areas only and the light areas may be ignored as intentional, as in the case of the graphic mark 46, or dust or powder.

Thus, with the gray scale image of FIG. 4, a simple threshold will separate the defects and the regular surface depressions from the other, bright features. For example, a threshold at 150, which would ignore all features brighter than gray scale value 150, would eliminate the mark 46 from analysis. Thus, since features with a brightness above this threshold may be ignored as intentional or easily removable, only the dark gray scale values need to be addressed. It is apparent that a second segmentation is needed to separate the defects from the intentional depressions. However, a different approach is taken with the present invention.

To fully understand the transformation of a gray scale image into a negative ideal mask a brief background in mathematical morphology is helpful.

MATHEMATICAL MORPHOLOGY

Mathematical morphology essentially comprises the two branches of integral geometry and geometrical probabilities. The notion of a geometrical structure is not purely objective. Mathematical morphology quantifies this intuition by introducing the concept of structuring elements. Chosen by the morphologist, they interact with the object under study, modifying its shape and reducing it to a sort of caricature which is more expressive than the actual initial phenomenon. The power of the approach, but also its difficulty, lies in this structural sorting.

Here, an introduction will be given to mathematical morphology in Euclidian space, where most of the properties of morphology will be given. Then mathematical morphology in binary digital space will be discussed. Finally, the subject will be reviewed in 3-dimensional space. It will be appreciated that the discussion given here is necessarily brief, but will enable one skilled in the art to understand the invention. For further reference, see Matherton, George, *Random Sets and Integral Geometry*, Wiley, 1975 and Serra, Jean, *Image Analysis and Mathematical Morphology*, Academic Press, 1982.

1. Euclidean Morphology

Let $E^n$ denote the set of all points in Euclidean n-space and let $p=(x_1, x_2, \ldots, x_n)$ represent a point of $E^n$. With each set A belonging to $E^n$ is associated a binary image A, an n-dimensional composition in black and white, where $(x_1, x_2, \ldots, x_n)$ is black in A if and only if $(x_1, x_2, \ldots, x_n) \in A$ otherwise $(x_1, x_2, \ldots, x_n)$ is white. Hereinafter, there will be no distinction between the image A and the set A, they will both be denoted by A. A binary image in $E^2$ is a silhouette, a composition in black and white which partitions the plane into regions of foreground (black) and background (white). A binary image in $E^3$ is a partitioning of a volume into points belonging to the surface and interior of objects (black)

and points belonging to the space surrounding those objects (white). Binary images in higher dimensions can be considered also.

1.1 Inclusion and Equality of Binary Images

Let A and B be any two binary images. If every black point of A is black in B, then A is called a Subimage of B, or A is included (contained) in B. Symbolically, this relation is denoted (Inclusion) $A \subseteq B \rightleftarrows a \in A \rightarrow a \in B$ The following are some properties of binary image (set) containment for any binary A, B and C:

(Reflexivity) $A \subseteq A$
(Transitivity) $(A \subseteq B)$ and $(B \subseteq C) \rightarrow A \subseteq C$
(Equality) $A = B \rightleftarrows A \subseteq B$ and $B \subseteq A$ A binary image is universal if it contains every binary image under discussion. The universal image which is all black is symbolized by $\Omega$. The all white binary image, or null image or blank image, does not contain any other binary images and is symbolized by $\phi$.

1.2 Logical Operation on Binary Images

This section introduces some basic operations on binary images. Using these operations, we can construct new binary images by combining the black points of given images following certain logical rules.

The intersection of two binary images A and B, written A ∩ B, is the binary image which is black at all points p which are black in both A and B. Symbolically (Intersection) $A \cap B = \{p \mid p \in A$ and $p \in B\}$ From the definition of intersection, it follows:

$A \cap B = B \cap A$
$A \cap A = A$
$A \cap \phi = \phi$

Since A ∩ B is a binary image, we can consider its union with another binary image C, (A∩B) ∩C={p |p ∈(A∩B) and p∈C}
We can show that $(A \cap B) \cap C = A \cap (B \cap C) = A \cap B \cap C$ For an indexed set of binary images $A = \{A_1, A_2, \ldots, A_n\}$ we write $A_1 \cap A_2 \cap \ldots \cap A_n = \cap_{i=1,n} A_i$ Similarly, the union of two binary images A and B, written A∪B, is the binary image which is black at all points p which are black in either A or B. Symbolically (Union) $A \cup B = \{p \mid p \in A$ or $p \in B\}$ From this definition we get the following properties:

$A \cup B = B \cup A$
$A \cup A = A$
$A \cup \phi = A$

Since A ∩ B is a binary image, we can consider its union with another binary image C, (Union) $(A \cup B) \cup C = \{p \mid p \in (A \cup B)$ or $p \in C\}$ we can show that (Associativity) $(A \cup B) \cup C = A \cup (B \cup C) = A \cup B \cup C$ For an indexed set of binary images $A = \{A_1, A_2, \ldots, A_n\}$ we write $A_1 \cup A_2 \cup \ldots \cup A_n = \cup_{i=1,n} A_i$ Let $\Omega$ be the universal binary image (all black) and A a binary image. The complement of A denoted A' is the binary image which interchanges the colors black and white in A. Symbolically, (Complement $A' = \{p \mid p \in \Omega$ and $p \notin A\}$

1.3 Geometric Operations of Dilation and Erosion

Let $p = (x_1, x_2, \ldots, x_n)$ and $q = (y_1, y_2, \ldots, y_n)$ denote two elements of $E^n$. The sum $p + q$ is the point (Sum) $p + q = (x_1 + y_1, x_2 + y_2, \ldots, x_n + y_n)$ while the difference $p - q$ is the point (Difference) $p - q = (x_1 - y_1, x_2 - y_2, \ldots, x_n - y_n)$ both in $E^n$. Is s is a real number, then (Scaling) $sp = (sx_1, sx_2, \ldots, sx_n)$ also belongs to $E^n$ and is referred to as scaling by s.

If A is a subimage of $E^n$ and p is a point in $E^n$, then the translation of A by p is a subimage of $E^n$ given by (Translation) $A_p = \{a + p \mid a \in A\}$ Translation of a binary image A by a point p shifts the origin of A to p.

We are now ready to define the two basic morphological operations of dilation and erosion. If $A_{b1}, A_{b2}, \ldots, A_{bn}$ are translations of the binary image A by the black points of the binary image $B = \{b_1, b_2, \ldots, b_n\}$ then the union of the translations of A by the black points of B is called the dilation of A by B and is symbolized by (Dilation) $A \oplus B = A_{b1} \cup A_{b2} \cup \ldots \cup A_{bn} = \cup_{b_i \in B} A_{b_i}$ Dilation is also called Minkowski addition.

Dilation can also be expressed in terms of the sums of points in binary images A and B, $A \oplus B = \{p \mid \exists_{b_i \in B} p \in A_{b_i}\} = \{p \mid \exists_{b_i \in B} \exists_{a_j \in A} p = a_j + b_i\}$ The operational dual of dilation is erosion. The erosion of a binary image A by a binary image B is black at a point p if and only if the translation of B to p is entirely contained in A. Symbolically, (Erosion) $A \ominus B = \{p \mid B_p \subset A\}$ Erosion is also called Minkowski subtraction.

Dilation can also be expressed in terms of the differences of points in binary images A and B, $$A \ominus B = \{p \mid \bigvee_{b_i \in B} b_i + p \in A\} = \{p \mid \bigvee_{b_i \in B a_j \in A} p = a_j - b_i\}$$

The dual nature of dilation and erosion is geometric rather than logical and involves a geometric negation as well as a logical negation. The geometric negation of a binary image is called its reflection. The reflection of a binary image B is that binary image B which is symmetric to B about the origin, that is (Reflection) $\breve{B} = \{-p \mid p \in B\}$ The geometric duality is expressed as $(A \oplus B)' = A' \ominus \breve{B}$ and $(A \ominus B)' = A' \oplus \breve{A}$ so that dilation and erosion can be expressed as $A \oplus B = \{p \mid \breve{B}_p \cap A \neq \phi\}$ and $A \ominus B = \cap_{x \in B} A_x$

1.4 Properties of the Geometric Operation

In the preceding section, we introduced the binary operations on binary images, dilation and erosion, and a unary operation, reflection. In this section, we will examine some properties which arise in the geometric operations.

First, let us present some basic identities for the geometric operation of dilation. For any binary images A, B and $C \in E^n$ we have:

(Commutativity) $A \oplus B = B \oplus A$
(Associativity) $(A \oplus B) \oplus C = A \oplus (B \oplus C) = A \oplus B \oplus C$ There exists a distinguished binary image $I \in E^n$ such that for any $A \in E^n$:

(Identity image) $A \oplus I = I \oplus A = A$

The identity image is black only at the origin of $E^n$.

Dilation distributes itself over union $A \oplus (B \cup C) = (A \oplus B) \cup (A \oplus C)$ but not over intersection.

So dilation is commutative, associative, distributive over union and possesses an identity element. Erosion is not commutative, since the erosion of A by B indicates the containment of B in A. But both $A \subset B$ and $B \subset A$ implies $A = B$. Hence, erosion does not commute except in the special instance $A = B$. But we have the following property, $(A \ominus B) \ominus C = (A \ominus C) \ominus B$ so that the order in which the erosion of A by B and C is applied is immaterial. More significant is the statement that erosion by a binary image which is itself the dilation of two binary images is equal to the sequential erosions by the factors of the eroding image. Symbolically, $A \ominus (B \oplus C) = (A \ominus B) \ominus C$ With respect to the distribution of erosion with the logical operations, we have:

$A \ominus (B \cup C) = (A \ominus B) \cap (A \ominus C)$ and $(B \cap C) \ominus A = (B \ominus A) \cap (C \ominus A)$ Finally, there exists a right identity element I for erosion, $A \ominus I = A$ but not a left identity.

1.5 Geometric Operations of Opening and Closing

We have from the preceding paragraphs definitions of the geometric operations on binary images which involves translating or sliding a reference binary image B, called a structuring element or its reflection, over a binary image A, the binary image under investigation or active binary image, for which any black point of the reflected binary image B overlaps any black point of A (dilation) or noting the positions of the origin of B for which the entire black region of B fits inside the black region of A (erosion). From these geometric interpretations of erosion and dilation, we draw definitions for two new binary operations on binary images which are expressible in terms of erosion and dilation.

First, the opening of a binary image A by a binary image B is the union of all translations of B which are included in A. Symbolically denoting the opening of A by B as $A_B$, we can write $A_B = \cup_{p \in (A \ominus B)} B_p$ since $p \in (A \ominus B)$ if and only if $B_p \subset A$. Now the union of all translations of a binary image B by the black points of a binary image $(A \ominus B)$ is by definition the dilation of B by $(A \ominus B)$. Since dilation is commutative, we can then write (Opening) $A_B = (A \ominus B) \oplus B$ Closing is the dual operation of opening and is most easily expressed in terms of the complement of A and the reflection of B. The complement of the closing of A by B is in union of all translations of B which are included in A'. Denoting the closing of A by B symbolically as $A^B$, we can write $(A^B)' = \cup_{p \in (A' \ominus \breve{B})} B_p$ since $p \epsilon (A' \ominus B)$ if and only if $B_p \subset A'$. Now the union of all translations of a binary image B by $(A' \ominus B)$ is the dilation of B by $(A' \ominus B)$. Since dilation is commutative, we can then rewrite the above equation as $$(A^B)' = (A' \ominus B) \oplus B$$

or simply $$(\text{Closing}) \ (A^B) = (A \oplus B) \ominus B$$

The duality of opening and closing is most easily expressed by the pairs of identities $$(A_B)' = (A')^B$$

and $$(A^B)' = (A')_B$$

In algebra, an application is said to be an opening if it is anti-extensive, increasing and idempotent. The operation of opening in the image algebra satisfies these three axioms. First, $X_B$ is anti-extensive, i.e., $$(\text{Anti-extensive}) \ X_B \subset X$$

since every point $x \epsilon X_B$ belongs to at least one translation of B included in X. Second, the opening is increasing, i.e., if X is included in Y then $X_B$ is included in $Y_B$, $$(\text{Increasing}) \ X \subset Y \to X_B \subset Y_B$$

and finally, we can show idempotence, i.e., $$(\text{Idempotent}) \ (X_B)_B = X_B$$

By duality, the closing $X^B$ is extensive, increasing and idempotent.

(Extensive)    $X \subset X^B$
(Increasing)   $X \subset Y \to X^B \subset Y^B$
(Idempotent)   $(X^B)^B = X^B$

1.6 Convex Binary Images

To this point, we have developed the concept of unary and binary operations on the set of all binary images in $E^n$. We now introduce the set of convex binary images in $E^n$ and develop some additional identities for this important case.

A binary image A in $E^n$ is convex if it contains the whole of every line segment joining any two of its points. If $a_1$ and $a_2$ are two points in A, then points x belong to the line segment joining them having the form $$x = sa_1 + (1-s)a_2 \tag{1}$$

where s is a scalar in the closed interval $0 \leq s \leq 1$. If there exists an s in the closed interval $[0,1]$ such that the equation above holds true, then we say that x is a convex combination of the points $a_1$ and $a_2$. Thus, a binary image A is convex if and only if for every point $x \epsilon A$ there also exists points $a_1$ and $a_2 \epsilon A$ such that x can expressed as a convex combination of $a_1$ and $a_2$.

This definition of a convex set is easy to understand and visualize. But it has no counterpart in the digital space where we replace the continuum $R^n$ by a lattice $Z^n$. A second definition of convex binary image can be extended to digital space.

A binary image X is convex if and only if it is the intersection of all half-spaces that contain it. Recall that a half-space $\pi$ of $E^n$ are points x which satisfy the relationship $$c_0 + c_1 x_1 + \ldots + c_n x_n \leq 0$$

Denoting the set of all convex binary images as C, we can formalize these two definitions of convexity as $$X \epsilon C \rightleftharpoons x_1, x_2 \epsilon X \to [x_1, x_2] \epsilon X$$

where $[x_1, x_2] = \{x \mid x \text{ is a convex combination of } x_1 \text{ and } x_2\}$ and $$X \epsilon C \rightleftharpoons X = \cap_i \pi_i, \pi_i \supset X$$

where the $\pi_i$ are the halfspaces of $E^n$.

1.7 Convex Hull

If A is a binary image in $E^n$, then the convex hull of A is that binary image in $E^n$ whose black points are those that can be expressed as convex combinations of the black points of A. A convex combination of the m points $a_1, a_22, \ldots, a_m$ of a binary image A is a point given by $$p = \Sigma_{i=1,m} s_i a_i \tag{2}$$

where the scalars $s_i$ are real numbers in the range $0 \leq s_i \leq 1$ and $\Sigma_{i=1,m} s_i = 1$. The expression of equation 1 is a special case of equation 2 for $m=2$. Thus, the convex hull of a binary image is black at a point p if and only if there exists black points $a_1, a_2, \ldots, a_m \epsilon A$ for some $m > 0$ and scalars $s_1, s_2, \ldots, s_m$ in the interval $[0,1]$ whose sum is unity such that p is expressible in the form of equation 2 above. The convex hull of a binary image A will be denoted C(A). Symbolically, $C(A) = \{p \mid p = \Sigma_{i=1,m} s_i a_i, 0 \leq s_i \leq 1, \Sigma_{i=1,m} S_i = 1, m > 0, a_i \epsilon A\}$ We can also say that the convex hull is the intersection of all the half-spaces that contain A. For both definitions, the convex hull is the smallest convex set that contains A, and is identical to A if A is convex.

If A is a binary image and B is a bounded binary image, then $$A^B \subset C(A)$$

If A is convex, then it is identical to its closure:

$$A \epsilon C, B \text{ bounded } \to A^B = A$$

1.8 Pseudo-Convex Hull

Now we have defined the convex hull of a binary image A as the intersection of all the binary halfspaces of $E^n$ that contain A, and more precisely as the intersection of <all the supporting half spaces of A in E.n Denote by H the halfspace of $E^n$ which satisfies the equation $$a_0 + a_1 x_1 + a_2 x_2 + \ldots + a_n x_n \leq 0$$

that is, H is a halfspace whose boundary with H' is the hyperplasia $$a_0 = a_1x_1 + a_2x_2 + \ldots + a_nx_n = 0$$

Now if $\{H_i\}$ is a finite set of such halfspaces containing n elements, then the pseudo-convex hull of a binary image A is $$C_p(A) = \cap_{i=1,n} A \oplus H_i$$

A regular n-hull of a binary image A in $E^2$ can be expressed as the intersection of the $A \oplus H_i$'s, where the $H_i$'s are translations of halfspaces defined from hyperplasias drawn through the origin and a vertex of a regular n-sided polygon centered at the origin.

2. Grayscale Morphology

Let $y = f(x)$ denote the grayvalue of a given point $x = (x_1, x_2, \ldots, x_n)$ in n-space, where the $x_i$ are the projected lengths of x on the basis vector $\vec{v}_i$, $i = 1, 2, \ldots, n$. The given point $[x, f(x)]$ can be represented in an augmented space for which the set of basis vectors $\vec{v}_i$ is extended by $\vec{v}_{n+1}$. The given point is represented by an $(n+1)$-tuple $x^* = (x_1, x_2, \ldots, x_n, x_{n+1})$ where $x_{n+1} = y$, the grayvalue of the point x in n-space.

If A is a set of points in n-space and if $f(x)$ is a function which assigns a grayvalue y to each point x of A, then A is a grayvalued image having a binary image representation in $(n+1)$-space, that is, the grayvalued image A in n-space corresponds to a binary image $A^*$ in $(n+1)$-space, where $x^* = (x_1, x_2, \ldots, x_n, x_{n+1})$ is an element of $A^*$ if and only if $x = (x_1, x_2, \ldots, x_n)$ is an element of A and the grayvalue $f(x) = x_{n+1}$. We say that $x^*$ has the value 1 if $x^* \epsilon A^*$ and zero otherwise in keeping with binary image convention.

Thus, a grayvalued image in 2-space can be denoted by a binary image in 3-space. The binary image in 3-space consists of black "sheets" not necessarily connected, representing the single valued function of grayvalue. In this form, the binary image is referred to as a grayvalued surface.

We could apply the functions of image algebra directly to grayvalued surfaces, but to do so would be analogous to restricting ourselves to line drawings in 2-space. Since we prefer to deal with foreground-background representation in 2-space where foreground, or black region, has solid form, we also prefer to deal with the binary image representation of a grayvalued image in solid form. For this reason, we introduce the concept of an umbra.

If A is a grayvalued image in n-space and $A^*$ is its grayvalued surface in $(n+1)$-space, then the umbra of A, denoted U(A), is a binary image in $(n+1)$-space where $$U(A) = A^* \oplus V_{n+1}$$

where the binary image $V_{n+1}$ is the reflection of $V_{n+1}$, the binary image representation of the positive $V_{n+1}$ axis. Thus, a point $q = (x_1, x_2, \ldots, x_n, x_{n+1})$ is black in the umbra representation of a grayvalued image if and only if the grayvalue of the point $x = (x_1, x_2, \ldots, x_n)$ in the corresponding grayvalued image is less than or equal to $x_{n+1}$. For $n = 2$, we have $$p = (x, y, z) \epsilon U(A) \rightleftharpoons z \leq f(x, y)$$

The significance of the umbrae for image processing is that they remain umbrae under the usual morphological transformations of union and intersection, dilation and erosion. The equivalence of grayscale images and umbrae allows us to speak morphologically of dilating or eroding a grayscale image by three dimensional structuring elements, because the dilation or erosion of an umbra by any set of 3-space is always an umbra. The operations of opening and closing a grayscale image can be represented by the sliding of 3-dimensional structuring elements over gray level topologies describing image density or brightness.

Morphological transformations are always expressible in terms of the operation of intersection, union, complementation, and translation. Intersections and unions of umbrae are umbrae. The height of the umbra union is the maximum of the individual umbrae. Symbolically, if $a(x)$ and $b(x)$ represent two gray scale functions, then $$U[a] \cup U[b] = U[\max(a,b)]$$

The points of the grayscale image union are then the maxima of the individual grayscale images. Similarly, the height of the umbra intersection is the minimum of the individual umbrae. Symbolically, $$U[a] \cap U[b] = U[\min(a,b)]$$

The points of the grayscale image intersection are then the minima of the individual grayscale images.

The complement of an umbra is an umbra where the scene of up and down is reversed. Thus, in the grayscale morphology we simply replace the function $f(x)$ by $-f(x)$.

Finally, of course, umbrae remain umbrae under translation.

The notion of the inclusion of an umbra is also treated by the relationship of the magnitude of the grayscale function:

$$U[a] \subset U[b] \rightleftharpoons a(x,y) < b(x,y)$$

Dilating or eroding an umbrae by a structuring element yields an umbra. This result comes directly from definitions for dilation and erosion. The dilation of U[a] by B is the union of translations of U[a] by the points of B. At a given location (x,y) the gray levels $d(x,y)$ of the dilation are determined by the maxima of the translated umbrae U[a]. Although U[a] is translated by all the points of B, only those points on the surface of B can create maxima. The dilation of a grayscale image is computed then, as the maximum of the sum of gray levels of b(x,y), $$d(x,y) = \max_{i,j} 8 \, a(x-i, y-i) + b(i,j)]$$

The erosion of U[a] by B is likewise determined as a difference of the gray levels of b(x,y) and the points of a(x,y), the gray levels of the eroded image e(x,y) determined by the minimum over all the points of b(x,y), $$e(x,y) = \min_{i,j}[a(x-i, y-j) - b(i,j)]$$

The expression for grayscale dilation and erosion bear a marked similarity to the convolution integral frequently encountered in image processing, with sums and differences replacing multiplication and minimum and maximum replacing summation. Unlike the linear transformations of grayscale images, dilation and erosions are characterized by their non-invertibility. Grayscale dilations and erosions, like their binary counterparts, remove grayscale information. The transformations are referred to as increasing in that they preserve containment relationships, rather than linear, as they are not invertible. Image processing through iterative morphological transformations is a process of selective information removal where irrelevant image content is irrecoverably destroyed, enhancing the contrast of the essential image features.

INSPECTION INFORMATION MANIPULATION

Figure 5:
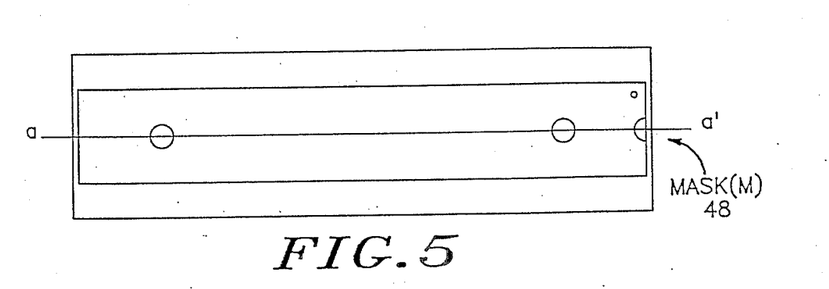
FIG. 5 is an illustration of a manipulated image taken from FIG. 3 for a non-defective package showing the expected areas of low reflectivity.
Figure 6:
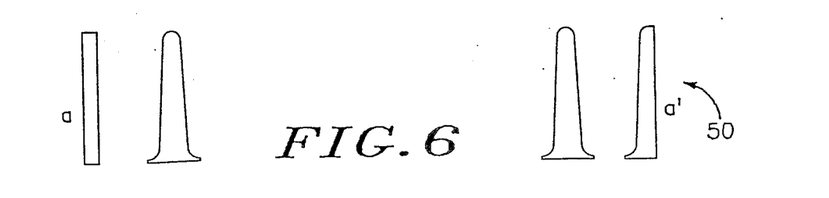
FIG. 6 is a schematic illustration of a negative ideal mask generated from the image of FIG. 5, where the areas of low light reflectivity are converted to areas of high value as a function of distance along the line a-a' of FIG. 5.

We now return to the inspection procedure, and how mathematical morphology may aid in that procedure. As noted, instead of segmenting the gray scale image of FIG. 4 further, the surface depressions are transformed to look like the regular surface before segmenting. To achieve this, a mask 48, such as that shown in FIGS. 5 and 6 is created during the learning phase.

Before inspecting the DIPs 24, a few known good samples are presented to the vision system to create a mask 48 and compute the threshold value.

Let $X_i$ denote the $i^{th}$ image learned. The $X_i$'s are transformed by Eq. 3 to get the mask 48 (M)

$$M_1 = [U_{i=1,n}\{((X_i)' - b)^A\}]^B \quad (3)$$

Where
b is a constant
A and B are three dimensional structuring elements
n is the number of parts learned in Eq. 3, $X_i$ is first complemented, then the highest value b, in the mark area 46 (defined as the areas between the mold marks 40) of the image complement, is subtracted from $X_i'$ to isolate the mold marks, pin one notch, and pin one dimple. This subtraction lowers every gray scale value by b, and sets all the negative numbers to zero. The next operation is a closing with structuring element A. Recall that a closing is a dilation followed by an erosion with the same structuring element A. In this case, A has a shape of a six-sided polyhedron; however, other shapes may be used. This closing eliminates the noise inherent to the image and flattens the tip of the mask. This is done on all of the parts learned. When all these images are obtained, their union is taken to include their maximum values. Another closing is then performed on that union with structuring element B to create an envelope around the image because closing has been shown to be extensive. In this case, B has the shape of a sphere.

FIG. 5 shows the resulting negative ideal mask. Shown in FIG. 6 is the profile 50 of the umbra along a-a' which shows the negative of the mold marks and the pin one notch. It also shows the negative of the area in front of and behind the package.

Another advantage of this method is of practical importance. If the mirrors or the light sources are moved by a small amount, the light intensity across the package will not be uniform, and a slightly darker area will be created to the right or left of the mark area. To compensate for these lower grayscale values, the mask image creates small grayscale values where the surface is darker. Note, however, that if the mirrors or the lights are moved by a large amount, the dark area will be inside the mark area. This will create an unusually low threshold, as computed in the next paragraph, which signals a problem.

To calculate the threshold, the histograms $h_{mi}(x)$ of the mark area for all the learned parts is computed. The mean m(x) and the standard deviation s(x) for each gray scale value x of the histograms are calculated by Eq. 4 and 5, respectively.

$$m(x) = [\Sigma_{i=1,n} h_{mi}(x)]/n \quad (4)$$
$$s(x) = \{\Sigma_{i=1,n}[h_{mi}(x) - m(x)]^2/(n-1)\}^{\frac{1}{2}} \quad (5)$$

where
n is the number of parts learned
x is the gray scale variable (x varies in [0,255])
$h_{mi}(x)$ is the histogram of the mark area of the $i^{th}$ part learned. The solution of Eq. 6 is the value of the threshold t used during the inspection.

$$\Sigma_{x=1,t} s(x) = k \quad (6)$$

where
k is a constant determined experimentally
t is the threshold.

To inspect a surface of an object, an image X is snapped. X is added to M from Eq. (3). Note that if the part is not oriented properly, the pin one notch 42 and pin one dimple 44 will be on the wrong side. These features will not be added to the proper values of the mask and remain dark areas. They are detected like all the other defects. The resulting gray scale image is then transformed into a two dimensional binary image B using Eq. 7

$$b(x,y) = 1 \text{ if } f(x,y) \leq t, \, 0 \text{ otherwise} \quad (7)$$

where
b(x,y) is the binary function of image B
f(x,y) is the gray scale image function
t is the threshold from Eq. 6

Figure 7:
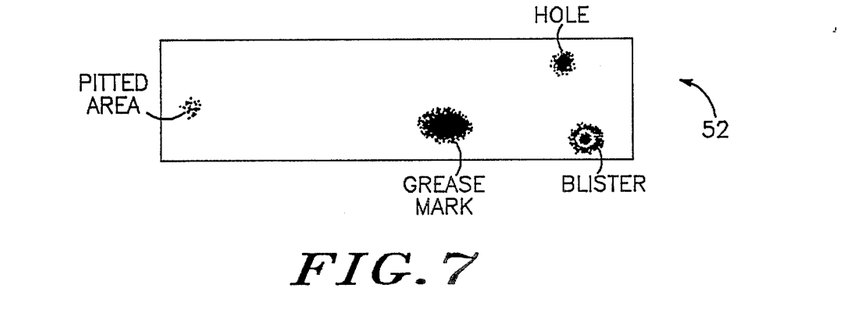
FIG. 7 is a schematic illustration of a map generated by adding the gray scale image of a surface being inspected to a negative ideal mask and then thresholding. The Figure shows how various defects might appear.

This transforms the gray scale image function f(x,y) into a binary function b(x,y) where the defects have a value of 1 and the regular areas a value of 0. If $B = \phi$ (empty set), then the surface is not defective, and the part is passed. This is a fast algorithm that takes 150 ms to run on the particular hardware used in this invention. Of course, the particular hardware or computer or processor used will vary in its run time for the algorithm. If defects are found as shown in the binary image with defects 52 in FIG. 7, then additional analysis needs to be performed. FIG. 7 illustrates how the binary image showing defects 52 would appear after the gray scale image, as in FIG. 4, is added to the mask 50 and thresholded.

For each defect, B will contain anywhere from a few non-connected points, e.g. a pitted surface, to a solid area with a jagged edge, e.g. a grease mark. Recall that a defect has to be larger than some dimension, d, determined from the specification, before the part is rejected. To do this measurement we need to create the regular 4-hull of each set and measure its height and width. But because the inspection only requires us to insure that the defects are larger than d before rejecting the part, we use Eq. 8 to transform the binary image into a simulated regular 4-hull.

$$Y = B^C$$

where
B is the original binary image
C is a two dimensional structuring element

Figure 8:
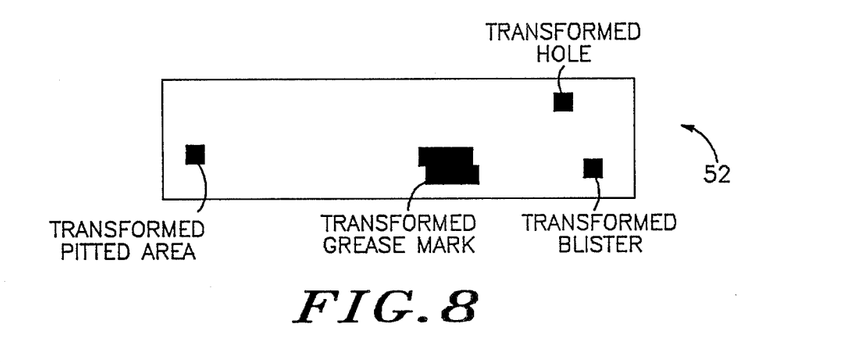
FIG. 8 is a binary image generated by transforming the image of FIG. 7 using morphological operations.

By closing the binary image with structuring element C, a square of w on a side, all the points in a neighborhood of size w are connected as shown in FIG. 8. Now if any of the defects are larger than the criteria specifies, the part is rejected.

To measure each connected component, the image is eroded as shown in Eq. 9.

$$Y = (X \ominus B_v) \cup (X \ominus B_h) \tag{9}$$

Where $B_h$ is a horizontal line of length d
$B_v$ is a vertical line of height d An image Y is then generated showing the defects over the prescribed size. If $Y \neq \phi$, then at least one of the defects is larger than the criteria specified and the part is rejected. Otherwise, the part is passed. In one embodiment, this additional processing adds up to 650 ms to the overall inspection time.

Figure 9:
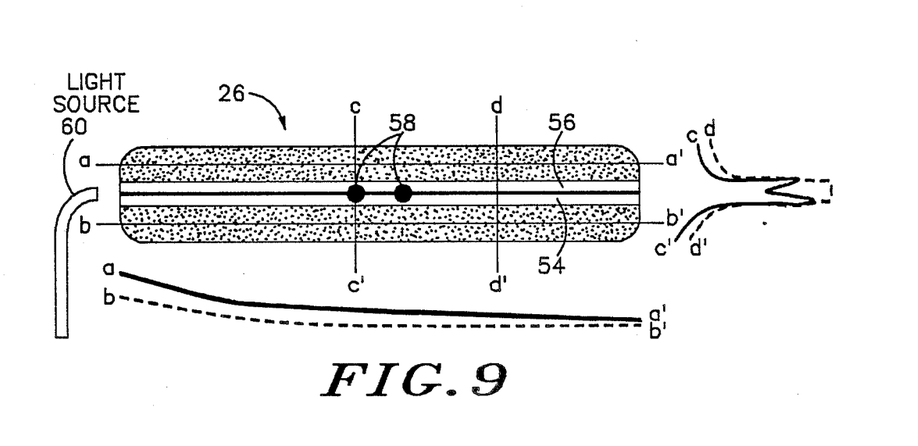
FIG. 9 is a schematic illustration of the end of an electronic package being inspected using the system of this invention taking into account certain unique features of the surface.

The tail and head of the package body 26 have a different profile than the top surface, but are inspected in a similar fashion. Shown in FIG. 9 is a schematic profile of the tail end of a package body 26. Plastic injection area 54 is a very rough and irregular surface; it is where the hot liquid plastic is injected into the mold. The mold flash 56 is where the top and the bottom halves of the mold meet when the parts are made. The heat sink holes 58, are formed by the heat sink inside the part. The angles that the sides of the top and bottom of the package body 26 tilt away from the plane of view can vary considerably. These surfaces may also be varied in their surface texture, which may be rough or smooth.

The variations on the end of the parts are irregular because they are not controlled properly during the molding process. For the defects to show up easily, low angular lighting is again needed. The light assembly 60 is only schematically illustrated in FIG. 9, but suggests that a fiber optic cable can be used to channel the light where it is desired. In one embodiment, even though the light intensity decreases with distance from the source, this may be compensated for during the learning process.

With this lighting, the profiles of the images are shown schematically in FIG. 9 across four different cross-sections. Note the non-uniformity of the light across the image in both directions (x and y). The light reflected from the plastic injection area 54 and the flash 56 is always bright. On the other hand, very little light is reflected from the heat sink areas 58. The reflectance from the remaining area depends on the finish as well as the distance from the light source. If it is a rough finish, the intensity is higher than if it is a smoother finish. For comparison purposes, using a 256 gray scale, the injection area 54 and the flash 56 have gray scale values of 230, the heat sink holes 58 have values around 90. It will be appreciated that the value scale is arbitrary and may contain more or less values than those used in this description. The light intensity on the remaining surface is not uniform along the width of the package and varies from 120 to 200.

The kinds of defects that occur on the tail and the head are similar to those described for the top of the package, except for a chip defect which occurs on the ends of the part. A chip defect is a very rough surface, which is seen as a bright area.

Learning the tail and the head of a package body 26 follows the same pattern as learning the top. A few parts are presented to the vision system, a mask and two thresholds are calculated, the high threshold is calculated for the chip defects and the low threshold for the other defects.

Let $X_i$ denote the ith image learned. The $X_i$'s are transformed by Eq. 10 to create another mask M.

$$M = [U_{i=1,n}[(X_i)_A]']B \tag{10}$$

Where

A and B are three dimensional structuring elements
n is the number of parts learned.

The raw image $X_i$ is opened with a three-dimensional structuring element A. The opening again creates an envelope around $X_i$. The resulting image is then complemented, and the union of all the learned images is taken. The final image is opened again with a three-dimensional structuring element B that creates the envelope of the union of the images.

The two thresholds are $t_h$ for the chips, and $t_l$ for the other defects. Once more, the mean m(x), and the standard deviation s(x) of the histograms are calculated using Eq. 11 and Eq. 12, respectively.

$$m(x) = [\Sigma_{i=1,n} h_i(x)]/n \tag{11}$$
$$s(x) = \{\Sigma_{i=1,n}[h_i(x) - m(x)]^2/(n-1)\}^{\frac{1}{2}} \tag{12}$$

Where $h_i(x)$ is the histogram of $U_{j=1,i}[(X_j)_A]' + X_i$. The high threshold is found by solving Eq. 13 for $t_h$ $$\Sigma i = t_h, 255^h(x) = k_h \tag{13}$$

While the low threshold $t_l$ is the solution of Eq. 14

$$\Sigma i = 0, t_l h(x) = k_l \tag{14}$$

Where $k_h$ and $k_l$ are constants determined experimentally.

Inspecting these end surfaces is similar to inspecting the top surface. An image is snapped and added to the background M from Eq. 10. The two thresholds are used to transform the gray scaled image function f(x,y) into a binary image function b(x,y). Eq. 15 is used for this segmentation.

$$b(x,y) = 0, \text{ if } t_l \leq f(x,y) \leq t_h \text{ or } 1, \text{ otherwise} \tag{15}$$

The algorithms of the top and bottom are repeated to find the defects and measure their sizes.

From the above, we should notice that the learning algorithms are more elaborate and therefore more time consuming than the inspections. This was purposefully done because the learning algorithm is performed on a few parts, for example about 7 to 15, while the inspection is done on thousands of parts for every lot.

I claim:

1. A method for inspecting surfaces of objects to determine whether the objects, the surfaces of which may include defective areas, a predetermined standard, comprising:

individually providing the objects having surfaces to be inspected to an inspection station;
    illuminating the surface including any defective areas thereon with a low angular light source;
    perceiving, by means of an imaging device, a gray scale image of the illuminated surface;
    adding the gray scale image to a negative ideal mask to form a combined gray scale image;
    generating a binary image of the combined gray scale image showing the defective areas of the combined gray scale image which exceed a brightness threshold;

transforming the binary image with defects using mathematical morphology into an image having simulated regular 4-hulls corresponding to the defective areas;

determining whether the simulated regular 4-hulls on the image are larger than a predetermined specification under the predetermined under the predetermined standard; and sorting the objects having surfaces the meet the predetermined specification from the objects having surfaces that do not meet the predetermined specification.

2. The method of claim 1 wherein the surface being inspected is a flat surface on an electronic package.

3. The method of claim 1 wherein the step of perceiving the gray scale image is performed by a computer imaging system that receives a digital array of gray scale pixels where the computer imaging system additionally adds the gray scale image to the negative ideal mask.

4. The method of claim 3 further comprising producing the negative ideal image from a morphological transformation of gray scale images of surfaces of a plurality of objects known to meet the predetermined standard.

5. A method for inspecting the surface of objects to determine whether the objects, the surfaces of which may include defective areas, meet a predetermined standard, comprising:

individually providing the objects having a surface to be inspected to an inspection station;

illuminating the surface including any defective areas thereon with a low angular light source;

perceiving, by means of an imaging device, a gray scale image of the illuminated surface;

providing a negative ideal mask from a morphological transformation of gray scale images of surfaces of a plurality of objects known to meet the predetermined standard;

adding the gray scale image to the negative ideal mask to form a resulting gray scale image;

thresholding the resulting gray scale image to obtain a binary image showing the defective areas;

transforming the binary image with defects using mathematical morphology into an image having simulated regular 4-hulls corresponding to the defective areas;

determining whether the simulated regular 4-hulls on the image are larger than a predetermined specification under the predetermined standard; and sorting the objects having surfaces that meet the predetermined specification from the object having surfaces that do not meet the predetermined specification.

6. The method of claim 5 wherein the surface to be inspected is a flat surface on an electronic package.

7. The method of claim 5 wherein the step of perceiving the gray scale image is performed by a computer imaging system that receives a digital array of gray scale pixels where the computer imaging system additionally adds the gray scale image to the negative ideal mask.

8. A method for inspecting surfaces of electronic packages to determine whether the packages meet a predetermined standard, the surfaces containing normal features which meet the predetermined standard and possibly containing defective features which cause the surfaces to not meet the predetermined standard, the method comprising:

a procedure for learning the surface to be inspected, comprising:

individually providing the packages having surfaces known to meet a predetermined standard to an inspection station;

illuminating the surface with a low angular light source;

perceiving, by means of a computer imaging system, a digital array of gray scale pixels;

calculating a brightness threshold, for the digital array of gray scale pixels, above which the normal features exist and below which defective features exist;

providing a negative ideal mask from a morphological transformation of gray scale images of surfaces of a plurality of objects known to meet the predetermined standard; and a procedure of inspecting the surfaces of electronic packages, comprising:

individually providing the packages having surfaces to be inspected to an inspection station;

illuminating the surface with a low angular light source;

perceiving by means of a computer imaging system, a gray scale image that is a digital array of gray scale pixels;

adding the perceived gray scale image to the negative ideal mask;

thresholding the result from the previous addition, using the calculated brightness threshold to obtain a binary image showing the defective features;

transforming the binary with defects using mathematical morphology into an image having simulated regular 4-hulls corresponding to the defective features;

determining whether the simulated regular 4-hulls on the image are larger than a predetermined specification under the predetermined standard by using mathematical morphology; and sorting the packages having surfaces that meet the predetermined specification from the packages having surfaces with defects that exceed predetermined specification.

9. A method for rejecting an electronic package if a defect on a surface thereof exceeds a selected size, comprising the steps of:

illuminating said surface to highlight said defect;

developing a gray scale image of said surface;

providing a negative ideal mask from a morphological transformation of gray scale images of surfaces of a plurality of packages of acceptable quality;

combining said gray scale image and said negative ideal mask to enhance said defect;

thresholding the resulting gray scale image to obtain a binary image showing the defective areas;

transforming the binary image with defects using mathematical morphology into an image having simulated regular 4-hulls corresponding to said defect;

determining whether the simulated regular 4-hulls on the image are larger than said selected size; and rejecting said object if the size of said defect exceeds said selected size.

* * * * *

UNITED STATES PATENT AND TRADEMARK OFFICE
CERTIFICATE OF CORRECTION

PATENT NO.   :   4,972,493

DATED        :   November 20, 1990

INVENTOR(S)  :   EPHREM A. CHEMALY

It is certified that error appears in the above-identified patent and that said Letters Patent is hereby corrected as shown below:

COLUMN 18, LINE 57
In claim 1 preamble, line 3, insert --meet-- after "areas,"

COLUMN 20, LINE 36
In claim 8, line 40, insert --image-- after "binary".

Signed and Sealed this

Twenty-first Day of April, 1992

Attest:

HARRY F. MANBECK, JR.

*Attesting Officer*                *Commissioner of Patents and Trademarks*